United States Patent
Adamson

(10) Patent No.: US 9,607,383 B2
(45) Date of Patent: Mar. 28, 2017

(54) METHOD FOR RECORDING INDIVIDUAL THREE-DIMENSIONAL OPTICAL IMAGES OF A DENTAL OBJECT

(71) Applicant: DENTSPLY SIRONA Inc., York, PA (US)

(72) Inventor: Anders Adamson, Darmstadt (DE)

(73) Assignee: DENTSPLY SIRONA Inc., York, PA (US)

( * ) Notice: Subject to any disclaimer, the term of this patent is extended or adjusted under 35 U.S.C. 154(b) by 48 days.

(21) Appl. No.: 14/421,271

(22) PCT Filed: Aug. 14, 2013

(86) PCT No.: PCT/EP2013/066995
§ 371 (c)(1),
(2) Date: Feb. 12, 2015

(87) PCT Pub. No.: WO2014/027026
PCT Pub. Date: Feb. 20, 2014

(65) Prior Publication Data
US 2015/0206306 A1     Jul. 23, 2015

(30) Foreign Application Priority Data
Aug. 14, 2012 (DE) .................. 10 2012 214 467

(51) Int. Cl.
*G06K 9/00* (2006.01)
*G06T 7/00* (2017.01)
(Continued)

(52) U.S. Cl.
CPC ............ *G06T 7/0024* (2013.01); *A61B 5/004* (2013.01); *A61B 5/0088* (2013.01);
(Continued)

(58) Field of Classification Search
None
See application file for complete search history.

(56) References Cited

U.S. PATENT DOCUMENTS 6,771,809 B1* 8/2004 Rubbert .................. A61C 7/00
345/419
7,698,068 B2* 4/2010 Babayoff ........... A61B 1/00009
433/37

(Continued)

FOREIGN PATENT DOCUMENTS

WO      2010/077380      7/2010

OTHER PUBLICATIONS

International Preliminary Report on Patentability date Nov. 6, 2014, in PCT Application No. PCT/EP2013/066995.
(Continued)

*Primary Examiner* — Nancy Bitar
(74) *Attorney, Agent, or Firm* — David A. Zdurne; Douglas Hura; Leana Levin

(57) ABSTRACT

The invention relates to a method for recording individual three-dimensional optical images (2) to form a global image of a dental object (1) which is to be measured. After each individual image (2) is taken by means of a dental camera (3), a computer (8) automatically checks whether an overlapping area (5, 12) between the images which are to be combined meet the recording requirements determined for a correct recording. If the overlapping area (5) meets the recording requirements, the recording is carried out between the images (6, 7) to be combined and a first image sequence (9) is set in motion. Said images of the first image sequence (9) are subsequently combined to form a first cluster (23). If the overlapping area (12) of an image (13) does not meet the recording requirements, the first image sequence (9) is interrupted, an additional second image sequence (14) is automatically started with said image (13). Subsequently, the images of the second image sequence (14) are combined to form a second cluster (24).

20 Claims, 1 Drawing Sheet

(51) Int. Cl.
*A61C 9/00* (2006.01)
*A61B 5/00* (2006.01)

(52) U.S. Cl.
CPC .......... *A61B 5/4547* (2013.01); *A61B 5/7425* (2013.01); *A61B 5/7475* (2013.01); *A61C 9/0053* (2013.01); *A61B 2576/02* (2013.01); *G06T 2207/30036* (2013.01)

(56) References Cited

U.S. PATENT DOCUMENTS

| | | | | |
|---|---|---|---|---|
| 8,041,439 B2* | 10/2011 | Kopelman | ......... | A61C 13/0004 700/117 |
| 8,478,437 B2* | 7/2013 | Boyden | ..................... | A61F 2/06 623/1.1 |
| 8,885,036 B2* | 11/2014 | Graze | ................... | B07C 5/3422 348/86 |
| 2005/0283065 A1* | 12/2005 | Babayoff | ........... | A61B 1/00009 600/407 |

OTHER PUBLICATIONS

International Search Report mailed Dec. 20, 2013, International Application No. PCT/EP2013/066995.
Written Opinion of International Search Authority, International Application No. PCT/EP2013/066995.
Office Action issued in German Patent Application No. 10 2012 214 467.6, mailed Mar. 8, 2013.

* cited by examiner

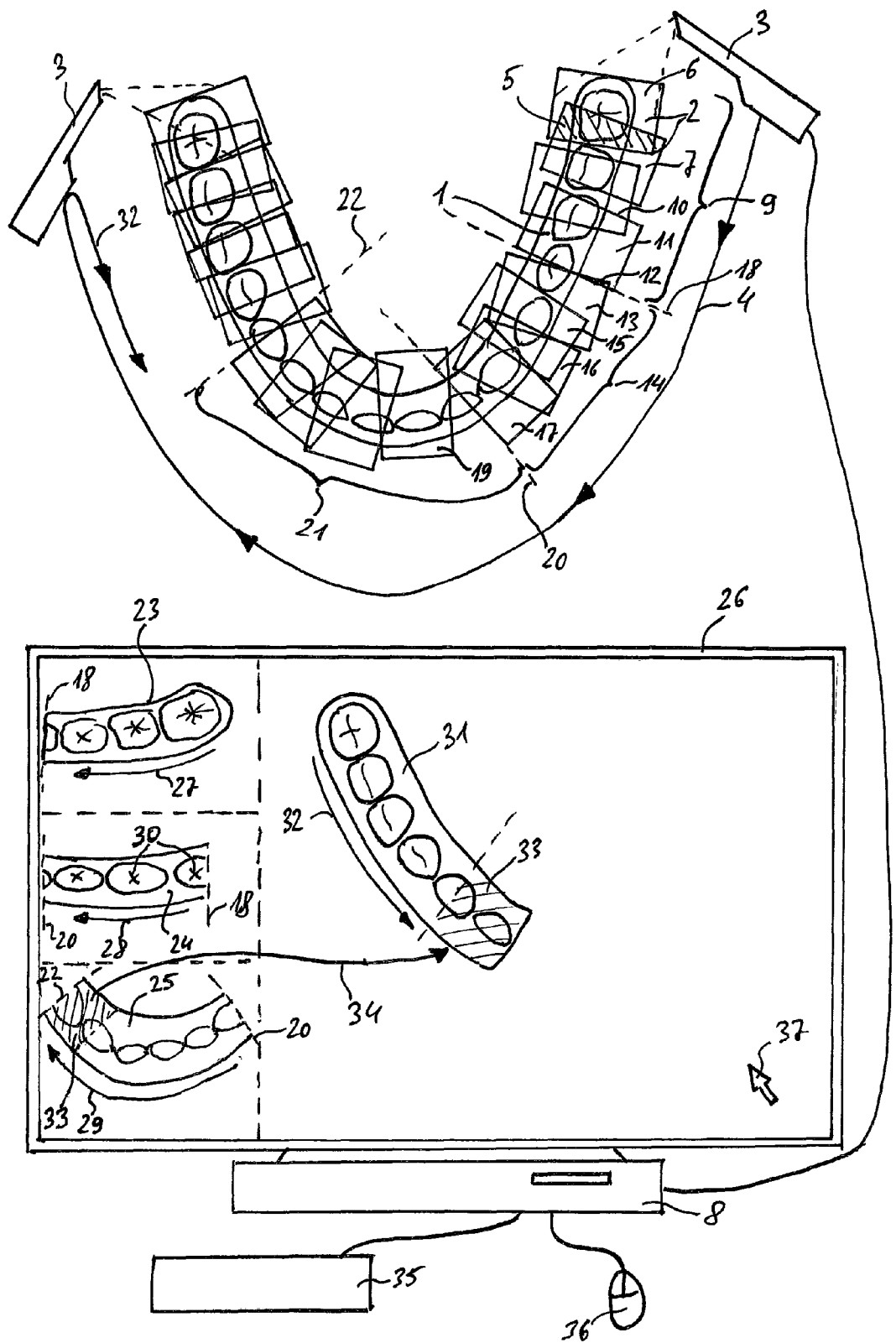

METHOD FOR RECORDING INDIVIDUAL THREE-DIMENSIONAL OPTICAL IMAGES OF A DENTAL OBJECT

CROSS REFERENCE TO RELATED APPLICATIONS

This application is a national stage entry of PCT/EP2013/066995 filed Aug. 14, 2013, which claims priority to German Patent Appln. No. 10 2012 214 467.6 filed Aug. 14, 2012.

BACKGROUND OF THE INVENTION

Field of the Invention

The invention relates to a method for recording individual three-dimensional optical images to form a global image of a dental object to be measured.

Description of the Related Art

Several recording methods are already known from the prior art in which several optical individual images are taken and then recorded. In the recording, matching areas, so-called overlapping areas, are detected and then recorded in relation to one another so that a global image is formed from the individual optical images.

When the individual images are combined, the recording may be flawed. This may for example be caused by overlapping areas that are too small, by mistakes in recording or by interfering objects, such as the tongue or cheek, in the recording area.

One disadvantage of such recording methods is that faulty dosing may result in a distorted three-dimensional image of the object and may thus cause mistakes in treatment.

Another disadvantage of this method consists of the fact that the entire measurement must be repeated if it is found that a recording is flawed.

The object of the present invention is therefore to provide a recording method that will permit a rapid and fault-free three-dimensional measurement of the dental object.

BRIEF SUMMARY OF THE INVENTION

The invention relates to a method for recording individual three-dimensional optical images to form a global image of a dental object to be measured, wherein a check is performed automatically after each individual imaging by means of a digital camera using a computer to ascertain whether an overlap area between the images to be combined fulfills certain recording conditions for a fault-free recording. If the overlapping area fulfills the recording conditions, then the recording is performed between the images to be combined, and a first image sequence is continued, whereupon the images of the first image sequence are combined to form a first cluster. However, if the overlapping area of an image does not fulfill the recording conditions, then the first image sequence is terminated and another second recording sequence is started automatically with this image, wherein the images of the second image sequence are combined to form a second cluster.

The optical images are measured by means of the dental camera which may function according to a fringe projection method, for example. In the fringe projection method, the individual strips projected onto the object may be identified on the basis of the intensity, color, polarization, coherence, phase, contrast, location or transit time. Then the 3D coordinates of the individual measurement points on the object are calculated using a triangulation method. In the color coding, each color strip can be identified unambiguously on the basis of a certain sequence of color strips. For the measurement, for example, a slide and/or grid with 140 color strips may be used, having a strip width of 130 μm in the measurement volume on the object. These color strips may have eight different colors, for example, where the sequence of a group of three color strips is unambiguous over 64 color strips.

During the measurement, the handheld dental camera is moved in relation to the dental object, such as a mandible or a maxilla, wherein the three-dimensional optical images are created at regular intervals. The individual images may be created with a frequency between 10 Hz and 20 Hz, for example. The recording is done by means of a computer that analyzes the images taken. For example, the ICP recording method (iterative closest point algorithm) may be used as the recording method. This algorithm is a known method for recording two-dimensional or three-dimensional objects. The goal of this method is to image two different 3D models of an object almost precisely over one another. To do so, different rotations and translations to corresponding point pairs of the two 3D models are used, and a quadratic error in the distances between the point pairs is thereby minimized. Therefore, in the first step, the closest neighbors to a certain point are ascertained. In the next step, the transformation to the recording is calculated. Next, the calculated transformation is applied to the point pairs to be recorded. This iterative approximation is carried out until the two 3D models correspond in the overlapping area.

Alternatively or additionally, the recording may also be made on the basis of the color of the recorded object, the surface curvature of the recorded object, or on the basis of geometric correspondences. In the recording on the basis of geometric correspondences, a pattern recognition algorithm is used in which the second image is searched for a certain geometric pattern, such as for an occlusal surface of a certain tooth, from the first recorded image.

A new cluster is started if the recording conditions for the overlapping area are not met. During the measurement of the dental object, a new cluster is thus started after each termination until the entire object has been measured. The individual clusters can then be combined to form the global image of the object. The recording conditions are not met, for example, in cases when the dental camera is moving too rapidly in relation to the object, and therefore the size of the overlapping area is inadequate. Another reason might be that an autofocus on the dental camera has a fuzzy setting, and therefore the object is imaged indistinctly so that the image quality of the image is inadequate. Another reason might be that moving objects such as the patient's tongue or the treating dentist's finger are detected during the measurement. As a result, the overlapping areas of the images do not match. The aforementioned reasons may thus lead to a termination of the image sequence.

One advantage of this method is that the recording conditions are checked after each imaging, thereby preventing a faulty recording.

Another advantage of this method is that the images already created are not discarded after a termination of the image sequence, but instead are combined to form a cluster. Then the individual clusters can be compared automatically and combined to form the global image of the object, so that individual areas of the dental object need not be measured repeatedly. The duration of the measurement is thereby shortened.

The recording conditions may advantageously include an adequate size of the overlapping area, an adequate waviness of the object surface in the overlapping area, an adequate roughness of the surface in the overlapping area, an adequate number of characteristic geometries in the overlapping area, and/or adequate image quality of the image in the overlapping area.

A faulty recording between the images to be combined is thereby prevented. A reliable recording is made possible due to the adequate brightness and roughness of the surface of the overlapping area, in contrast with a planar surface. The adequate number and arrangement of the characteristic geometries such as fissures or dental cusps, for example, also enable reliable recording. If the image quality is adequate, the dental object is imaged sharply and with a high contrast. One reason for low contrast might be inadequate lighting of the object. One reason for a blurred image might be, for example, an improperly adjusted autofocus.

The adequate size of the overlapping area may advantageously amount to at least one quarter of an image surface of the respective image.

A fault-free recording is ensured by such an overlapping area.

If multiple clusters are formed in multiple image sequences, the individual clusters may advantageously be combined into the global image of the object, wherein a check is automatically performed during the measurement at regular intervals, or automatically after the measurement, of whether a present cluster has a cluster overlapping area with the preceding clusters, and whether this cluster overlapping area fulfills the recording conditions.

Thus during the measurement, a current image of the previous image is recorded and added to the present cluster as long as the recording conditions are met and it does not result in a termination of the image sequence. During this addition, the present cluster is compared with the preceding clusters that were previously measured. In doing so, a check is performed of whether the present cluster has a cluster overlapping area with the preceding clusters, and whether this cluster overlapping area fulfills the recording conditions already used in recording the individual images.

The individual clusters are thereby automatically combined into the global image as soon as a sufficient cluster overlapping area is found. The clusters thus do not have to be combined manually, and the measurement duration is thereby shortened.

The present cluster is thereby compared with the preceding clusters in short intervals to find fitting cluster overlapping areas.

The check of the present cluster may advantageously be performed at regular intervals after every 10 to 40 images.

The growing present clusters are thereby compared with the preceding clusters at short intervals after every 10 to 40 images.

The check of the present cluster may advantageously take place once an area that has been added to the present cluster since a preceding check exceeds an area of at least 0.25 cm$^2$.

The check is therefore performed only when the added area exceeds at least 0.25 cm$^2$. This has the advantage that the check is performed only when the dental camera is moved in relation to the object.

The present cluster and the preceding clusters may advantageously be displayed graphically at the same time by means of a display device, wherein the combination of the individual clusters to form the global image of the object is performed during the measurement.

The preceding clusters already recorded and the present cluster are therefore displayed by means of the display device, such as by means of a monitor to give the user a better overview of the imaging situation or the imaging process. This allows the user to see, already during the measurement, which areas of the dental object have already been measured and which have not. The user could perform targeted measurements of areas situated between the clusters already recorded and to record the clusters with one another.

By displaying the added area of the present cluster, the user sees the direction in which the cluster is growing. Displaying the image direction of the individual clusters additionally facilitates orientation for the user in order to ascertain which areas of the dental object have not yet been measured. Displaying the termination allows the user to ascertain at which location the respective cluster was terminated. The user could thus move the present cluster specifically in the direction of a termination point of the previous clusters in order to create an adequate cluster overlapping area.

The added area of the present cluster, an image direction of the individual clusters and/or the position of a termination of the clusters already recorded can advantageously be displayed graphically by means of the display device.

Displaying the image seal and the termination positions makes it possible for the user to gain a better overview of the imaging process.

The recording of the individual clusters may advantageously occur during the measurement of the object without putting the camera down.

Therefore, the measurement of the object is performed continuously, with a new cluster being formed after each termination.

The recording of the images and/or the clusters may advantageously take place using semantic structures, namely on the basis of the determined contour of a dental arch to be measured, a direction of occlusion and/or on the basis of tooth centers.

The semantic structures can be recognized by using a database that includes multiple datasets of dental arches, teeth and occlusal surfaces of various patients. On the basis of this additional information, the positional relationship between the images to be combined is checked, and the recording is thereby improved. The additional information based on the semantic structures also simplifies the mathematical recording problem, thereby shortening the computation time.

The direction of occlusion can be advantageously determined automatically by means of the computer by using an analytical method on the images recorded, wherein surface normals are generated from the tooth surfaces of the measured teeth of the object, and an average of the surface normals of an occlusal surface forms the direction of occlusion of a certain tooth.

The direction of occlusion is determined automatically in this way by using the analytical method.

The recording of the images and/or the clusters may take place automatically by using image field recording, wherein the images or clusters that have been combined are subdivided into multiple subareas with a defined size, and then the subareas are compared according to a fixed sequence to find the overlapping area or the cluster overlapping area that satisfies the recording conditions.

Therefore only the small subareas are compared with one another, so that the computation time for the recording is thereby shortened.

BRIEF DESCRIPTION OF THE DRAWINGS

The invention will now be explained with reference to the drawings.

FIG. 1 shows a diagram to illustrate the present method of recording the individual images.

DETAILED DESCRIPTION OF THE INVENTION

FIG. 1 shows a diagram to illustrate the present method of recording individual images of a dental object 1 to be measured, such as a mandible. The three-dimensional optical images 2, which are illustrated in the form of rectangles, are measured by means of a dental camera 3 which is moved relative to the object 1 along a measurement path 4 during the measurement. The dental camera 3 may be a handheld camera, for example, which measures the object 1 using a fringe projection method. A first overlapping area 5 between a first image 6 and a second image 7, which is shown with a dashed line, is checked with regard to the recording conditions by using a computer 8. A check is performed of whether the overlapping area is of an adequate size, having an adequate waviness, an adequate roughness, an adequate image quality and/or an adequate number and arrangement of characteristic geometries. For example, a check can be performed of whether the overlapping area amounts to at least one-fourth of the surface area of the first image 6. The first overlapping area 5 fulfills the recording conditions so that a first image sequence 9 consisting of the first image 6, the second image 7, a third image 10 and a fourth image 11 is continued. However, a second overlapping area 12 between the fourth image 11 and a fifth image 13 does not fulfill the recording conditions because the second overlapping area is too small. Then the first image sequence is terminated, and another, second image sequence 14 consisting of the fifth image 13, the sixth image 15, the seventh image 16 and the eighth image 17 is started automatically. The first termination 18 of the first image sequence 9 is represented by a dashed line. Between the eighth image 17 and a ninth image 19, there follows a second termination 20 of the second image sequence 14; then a third image sequence 21 is measured up to a third termination 22. The images of the first image sequence 9 up to a first cluster 23, the images of the second image sequence 14 up to a second cluster 24 and the images of the third image sequence 21 up to a third cluster 25 are combined by a computer 8. The clusters 23, 24 and 25 are displayed by means of a display device 26, such as by means of a monitor. To facilitate orientation, a first image direction 27, a second image direction 28 of the second cluster 24, and a third image direction 29 of the third cluster 25 are represented by arrows. In addition, semantic structures such as tooth centers 30 can also be displayed. The positions of the terminations 18 may also be displayed. Then a fourth present cluster 31 is measured in a fourth image direction 32. A check is performed automatically at regular intervals of whether the present cluster 31 has a cluster overlapping area 33, which is shown with dashed lines, with the previously recorded clusters 23, 24 and 25, and whether this cluster overlapping area 33 fulfills the recording conditions. This check may be performed, for example, at regular intervals after every 10 to 40 images. Next, a recording is made between the third cluster 25 and the fourth cluster 31, wherein the third cluster 25 is combined with the fourth cluster 31, as represented by the arrow 24. Additional clusters at the termination sites 18 and 20 may be measured in this way, and all the clusters 23, 24, 25 and 31 are combined into a global image of the object 1.

Alternatively, the individual clusters 23, 24, 25 and 31 may also be combined manually by the user into the global image by using input means such as a keyboard 35 and a mouse 36, by means of a cursor 37.

REFERENCE NUMBERS 1 object
2 image
3 camera
4 measurement path
5 first overlapping area
6 first image
7 second image
8 computer
9 first image sequence
10 third image
11 fourth image
12 second overlapping area
13 fifth image
14 second image sequence
15 sixth image
16 seventh image
17 eighth image
18 first termination
19 ninth image
20 second termination
21 third image sequence
22 third termination
23 first cluster
24 second cluster
25 third cluster
26 display device
27 first image direction
28 second image direction
29 third image direction
30 tooth centers
31 fourth cluster
32 fourth image direction
33 cluster overlapping area
34 arrow
35 keyboard
36 mouse
37 cursor

The invention claimed is:

1. A method of forming a combined three-dimensional image of one or more dental objects from a plurality of images, comprising the steps of:
   receiving a plurality of optical images, respectively corresponding to a plurality of different imaging positions, of one or more dental objects generated by a dental camera according to a recording sequence,
   wherein each optical image overlaps with another optical image to form a plurality of overlapping areas, and
   wherein each overlapping area includes a later optical image and an earlier optical image, the later optical image generated at a later imaging position in the recording sequence than the earlier optical image; and
   determining, for each overlapping area, whether the overlapping area fulfills one or more recording conditions, wherein for a first overlapping area:
   (i) adding the later optical image to an image sequence that includes the earlier optical image if the first overlapping area fulfills the one or more recording conditions, and
   (ii) adding the later optical image to a different image sequence from the image sequence that includes the earlier optical image if the first overlapping area does not fulfill the one or more recording conditions, optionally repeating steps (i) and/or (ii) for different overlapping areas of the plurality of overlapping areas; and combining the image sequence and the different image sequence to form the one or more global objects.

2. The method according to claim 1, further comprising: combining, for each image sequence, optical images included in the image sequence to form one or more image clusters.

3. The method according to claim 1, wherein the one or more recording conditions include: an adequate size of the overlapping area, an adequate waviness of an object surface in the overlapping area, an adequate roughness of the object surface in the overlapping area, an adequate number of characteristic geometries in the overlapping area, and/or adequate image quality in the overlapping area.

4. The method according to claim 3, wherein the adequate size of the overlapping area is one-fourth of an area of either the later optical image or the earlier optical image.

5. The method according to claim 2, further comprising: concurrently displaying the one or more image clusters on a display device.

6. The method according to claim 2, further comprising: combining the one or more image clusters to form a global image of the one or more dental objects.

7. The method according to claim 6, further comprising: displaying, on a display device, the global image of the one or more dental objects.

8. The method according to claim 2, further comprising: identifying one or more semantic structures in the plurality of optical images, wherein the combining of the optical images to form the one or more image clusters is based on the one or more semantic structures.

9. The method according to claim 8, wherein the one or more semantic structures include: a curve of a dental arch, directions of one or more occlusal surfaces respectively corresponding to one or more teeth, or one or more tooth centers respectively corresponding to the one or more teeth.

10. An apparatus, comprising:
a computer configured to:
receive a plurality of optical images, respectively corresponding to a plurality of different imaging positions, of one or more dental objects generated by a dental camera according to a recording sequence,
wherein each optical image overlaps with another optical image to form a plurality of overlapping areas, and
wherein each overlapping area includes a later optical image and an earlier optical image, the later optical image generated at a later imaging position in the recording sequence than the earlier optical image, and
determine, for each overlapping area, whether the overlapping area fulfills one or more recording conditions, wherein for a first overlapping area, the computer is further configured to:
(i) add the later optical image to an image sequence that includes the earlier optical image if the first overlapping area fulfills the one or more recording conditions, and
(ii) add the later optical image to a different image sequence from the image sequence that includes the earlier optical image if the first overlapping area does not fulfill the one or more recording conditions, optionally repeat steps (i) and/or (ii) for the different overlapping areas of the plurality of overlapping areas; and combine the image sequence and the different image sequence to form the one or more global objects.

11. The apparatus according to claim 10, wherein the computer is further configured to combine, for each image sequence, optical images included in the image sequence to form one or more image clusters.

12. The apparatus according to claim 10, wherein the one or more recording conditions include: an adequate size of the overlapping area, an adequate waviness of an object surface in the overlapping area, an adequate roughness of the object surface in the overlapping area, an adequate number of characteristic geometries in the overlapping area, and/or adequate image quality in the overlapping area.

13. The apparatus according to claim 12, wherein the adequate size of the overlapping area is one-fourth of an area of either the later optical image or the earlier optical image.

14. The apparatus according to claim 11, further comprising:
a display device, wherein the computer is further configured to cause the display device to display the one or more image clusters.

15. The apparatus according to claim 11, wherein the computer is further configured to combine the one or more image clusters to form a global image of the one or more dental objects.

16. The apparatus according to claim 15, further comprising:
a display device, wherein the computer is further configured to cause the display device to display the global image of the one or more dental objects.

17. The apparatus according to claim 11, wherein the computer is further configured to identify one or more semantic structures in the plurality of optical images, wherein the optical images are combined to form the one or more image clusters based on the one or more semantic structures.

18. The apparatus according to claim 17, wherein the one or more semantic structures include: a curve of a dental arch, directions of one or more occlusal surfaces respectively corresponding to one or more teeth, or one or more tooth centers respectively corresponding to the one or more teeth.

19. A method according to claim 1 further comprising:
determining a termination between a first image sequence, comprising a first subset of the plurality of images, and a second image sequence, comprising a second subset of the plurality of images different from the first subset of the plurality of images,
wherein the termination is between an image in the first image sequence and another image in the second image sequence that have an overlapping area less than a predetermined threshold;
generating a first three-dimensional image from the first subset of the plurality of images in the first image sequence;
generating a second three-dimensional image from the second subset of the plurality of images in the second image sequence; and
combining the first three-dimensional image and the second three-dimensional image to form a combined three-dimensional image.

20. The apparatus according to claim 10 wherein the computer configured to:
determine a termination between a first image sequence, comprising a first subset of the plurality of images, and a second image sequence, comprising a second subset of the plurality of images different from the first subset of the plurality of images,
wherein the termination is between an image in the first image sequence and another image in the second image sequence that have an overlapping area less than a predetermined threshold, generate a first three-dimensional image from the first subset of the plurality of images in the first image sequence, generate a second three-dimensional image from the second subset of the plurality of images in the second image sequence, and combine the first three-dimensional image and the second three-dimensional image to form a combined-three dimensional image.

* * * * *